United States Patent [19]
Bishko et al.

[11] Patent Number: 5,104,374
[45] Date of Patent: Apr. 14, 1992

[54] ELECTRONIC FLUID FLOW RATE CONTROLLER FOR CONTROLLING THE INFUSION OF INTRAVENOUS DRUGS INTO A PATIENT

[76] Inventors: Jay R. Bishko, 4204 Allistair Rd., Winston-Salem, N.C. 27104; Thomas G. Single, 3504 Joel Ct., Stone Mountain, Ga. 30087; Dennis Stone, 3908 State Road 13 North, Jacksonville, Fla. 32259

[21] Appl. No.: 465,758

[22] Filed: Jan. 16, 1990

[51] Int. Cl.⁵ .............................................. A61M 5/00
[52] U.S. Cl. ...................................... 604/31; 604/65; 128/DIG. 13
[58] Field of Search ............... 604/19, 21, 30, 31, 604/50–53, 65–67, 151, 246, 247, 189; 128/DIG. 12, 13; 364/413.01, 413.02, 413.04, 413.07, 509, 510

[56] References Cited

U.S. PATENT DOCUMENTS

| | | | |
|---|---|---|---|
| 3,655,095 | 4/1972 | Kienitz | 604/65 |
| 4,018,362 | 4/1977 | Ubaud . | |
| 4,321,461 | 2/1982 | Walter, Jr. et al. . | |
| 4,392,849 | 7/1983 | Petre et al. | 604/66 |
| 4,449,538 | 5/1984 | Corbitt et al. | 128/760 |
| 4,507,112 | 3/1985 | Hillel et al. . | |
| 4,585,441 | 4/1986 | Archibald . | |
| 4,589,372 | 5/1986 | Smith | 119/51 R |
| 4,623,331 | 11/1986 | Cewers et al. . | |
| 4,624,661 | 11/1986 | Arimond | 604/151 |
| 4,634,426 | 1/1987 | Kamen . | |
| 4,670,007 | 6/1987 | Wheeldon et al. . | |
| 4,710,163 | 12/1987 | Butterfield . | |
| 4,710,166 | 12/1987 | Thompson et al. . | |
| 4,731,051 | 5/1988 | Fischell . | |
| 4,756,706 | 7/1988 | Kerns et al. . | |
| 4,838,857 | 6/1989 | Strowe et al. | 604/67 |
| 4,898,578 | 2/1990 | Rubalcaba | 604/66 |

*Primary Examiner*—Stephen C. Pellegrino
*Assistant Examiner*—Steven J. Shumaker
*Attorney, Agent, or Firm*—Hopkins & Thomas

[57] ABSTRACT

An electronic controller connected to an electronic infusion pump which regulates the rate at which a drug is infused into a person. A magnetic card reader reads from a magnetic card, the name of the drug, the stock solution, concetration recommended dosage rate and warnings. The weight and the desired dosage rate of the patient is fed by a touch pad to the controller. The controller automatically computes the infusion rate and notifies via a display whether the desired rate exceeds the recommended rate. Also displayed are details about the drug, the length of time the patient has been infused, the amount of drug infused, and the dosage rate since the last rate change.

17 Claims, 3 Drawing Sheets

ELECTRONIC FLUID FLOW RATE CONTROLLER FOR CONTROLLING THE INFUSION OF INTRAVENOUS DRUGS INTO A PATIENT

BACKGROUND OF THE INVENTION

A. Field of the Invention

The present invention relates to an electronic fluid flow rate controller for controlling the infusion of intravenous (IV) drugs into a patient. More particularly the present invention discloses the use of a magnetic media reading means to read information from magnetic media about the IV drug to be infused.

B. Description of Prior Art

The use of electronic pumps to control the infusion of IV drugs is well known in the medical arts. Of late some of these electronic infusion pumps are even computer controlled. Despite these advances, current electronic infusion pump technology suffers from a number of disadvantages. Current electronic infusion pumps require a great deal of user knowledge. A user setting up an infusion generally needs to know the drug being infused, the stock solution concentration of the drug, warnings specific to the drug being infused, the desired dosage rate, the recommended dosage rate and the patient's body weight. The user must even calculate the infusion rate. Current electronic infusion pumps do not provide the user with this information, nor do they convert the desired dosage rate into an infusion rate. The large information burden placed upon a user frequently means that the help of other medical personnel must be sought to begin or check on an ongoing infusion.

SUMMARY OF THE INVENTION

The present invention overcomes the above mentioned disadvantages of the prior art. In particular, the present invention greatly reduces the information the user of an electronic infusion pump needs to set up or evaluate a drug infusion. The user interface guides the user through the infusion set-up. These advantages are achieved primarily through the use of a magnetic media reading means and the electronic controller, which greatly improves the user interface. The information read from the magnetic means includes the name of the drug to be infused, the stock solution concentration, the recommended dosage rate and any warnings specific to the drug. This information is conveyed by the magnetic media reading means to the electronic controller. A user of the present invention need only enter through a touch pad means the desired dosage rate and the patient's body weight, thus reducing the opportunity for human error. The electronic controller automatically calculates the infusion rate for the user and notifies the user via a display means should the desired dosage rate exceed the recommended dosage rate, again reducing the possibility of human error. Further, the invention provides such valuable information as the length of time the patient has been infused with the drug, the amount of the drug infused, current dosage rate and the time since the last infusion rate change.

As a further advantage, the invention can easily and inexpensively be added to existing infusion pumps which are designed for remote control.

DESCRIPTION OF THE PREFERRED EMBODIMENT

Turning now to the figures in which like numerals denote like parts, a preferred embodiment of the present invention may be seen.

Figure 1:
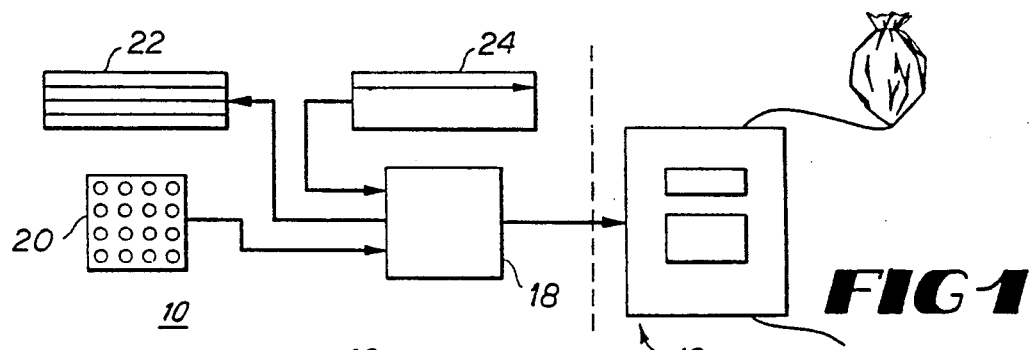
FIG. 1 is a block diagram of the present invention showing the interconnection between the various components.

As can be seen in FIG. 1, the Apparatus 10 of the present invention includes an electronic controller 18, connected to peripheral devices including an electronically controllable fluid dispensing means 12, a touch pad means 20, a display means 22 and a magnetic media reading means 24. The electronic controller 18 is electronically connected to all of the peripheral devices 12, 20, 22, 24 and all of the peripheral devices 12, 20, 22, 24, are electrically connected only to the electronic controller 18. The electronic controller 18 communicates with the magnetic media reading means 24 using a first communications link 14. The touchpad means 20 communicates with the electronic controller 18 using a second communications link 15. The electronic controller 18 communicates with the display means 22 via a third communications link 16. Finally the electronic controller 18 and the electronically controllable fluid dispensing means 12 exchange information via a fourth communications link 17.

The electronic controller 18 controls the flow of information between the peripheral devices 12, 20, 22, 24, as well as controlling the peripheral devices 12, 20, 22, 24. Additionally, the electronic controller 18 performs for the user all calculations necessary to begin infusion and provides a simple user interface. In the preferred embodiment, the electronic controller 18 is centered upon an 8 bit microcontroller. The 87HC51 is especially suited to be the electronic controller 18 of this invention because of its I/O capabilities: four 8 bit parallel I/O ports. The 87HC51's on board memory suffices for the application, thus eliminating any need for external memory. All software used in the preferred embodiment is resident on the 87HC51. The present invention can be practiced with any microcontroller, or digital or analog electronics capable of handling the I/O requirements of four peripheral devices and performing minor computations.

In the preferred embodiment, the magnetic media reading means 24 is a MAGTEK magnetic card reader. The magnetic card reader communicates with the electronic controller 18 via a serial link. The serial link operates at 1200 baud with even parity, one stop bit and 8 data bits.

The function of the magnetic media reading means 24 in the invention is to convey information to the electronic controller 18 about the IV drug to be infused. The information conveyed by the magnetic media reading means 24 includes the name of the IV drug, the stock solution concentration of the IV drug in mg per cc of liquid, the recommended range of dosage rates, and any warnings specific to that drug. This information is stored on magnetic media, or in the case of the preferred embodiment, magnetic cards (not shown). Previous inventions required that the user provide all this information and perform the calculation of the infusion rate. The use of magnetic media or cards to convey information to the electronic controller 18 reduces the possibility of human error and the information burden placed upon the user of the invention. The use of magnetic media to store this information means that the user of the invention need know only two pieces of information: the patient's body weight and the desired dosage rate. The use of magnetic media also means that use of the invention is not limited to any set of drugs. The invention may be used with any IV drug for which there is information stored on magnetic media or a magnetic card.

In the preferred embodiment, the, magnetic cards possess 3 tracks. Each tracks holds 80 characters. The data is stored on the cards in a format unique to this invention. Symbolically, this format can generally be represented in the following manner: % Drug:Name <00/000D5.W<00−00$0< WARNING<WARNING.

An example of that format follows:

For the drug, Sodium, Nitroprusside, a stock solution concentration of 50 milligrams in 250 cc of glucose water, recommended dosage rate of 0.5 to 10 micrograms per cc with warnings specific to this drug:

%SODIUM:NITROPRUSSIDE<50/250D-
5W<0.5−10$1<WRAP:IN:AL:FOIL<GOOD:-
FOR:24HRS:ONLY

Each symbol in the previous example has a specific meaning and must be used in that format in order for the apparatus to recognize the data properly. The '<' is used as a field separator, the ':' is used in place of one blank space, the '%' is used to symbolize the start of valid data. The '/' is used as it ordinarily would be used to mean 'per'. The '$' signified that the next character tells the units being used, and the '?' means end of data from the card. The units signifier is a $1 for micrograms/kilogram/minute; $2 for milligrams/kilogram/hour; $3 for micrograms/minute; and $4 for milligrams/hour.

Magnetic cards for IV drugs could be stored in a tray attached to the invention. Drug manufacturer's could provide the cards or the hospitals could make their own.

In the preferred embodiment, the electronically controllable fluid dispensing means 12 is an IVAC 560 infusion Pump, which is commercially available. The IVAC 560 includes a computer interface module, allowing remote operation and monitoring of the pump. The IVAC 560 is intended to be used as one of several pumps controlled by a single host control monitoring station. In this application, the electronic controller 18 simply acts as the host control station. As a result the invention can be easily and inexpensively retrofitted into current hospital infusion systems.

In the invention's preferred embodiment, the display means 22 is a commercially available Seiko liquid crystal display (LCD) module.

DETAILED DESCRIPTION OF METHOD OF USE

Upon power-up, the display means 22 will prompt the user to place a magnetic media or magnetic card into the magnetic media reading means 24.

The user will next press the number "1" on the touch pad means 20. This causes the display means 22 to prompt the user to enter the time and date.

The user need only enter the time and date when the system is powered on for the first time or to change the date and time. The user may input the time and date using the touch pad means 20. As a 24 hour clock is used in the electronic controller 18, the time and date must be entered in a specific numerical format: The first two digits represent the hour, ranging from 0-23, the next two digits represent minutes past the hour and they may range from 0-59. The third pair of digits is for the day of the month, ranging from 1-31 and the fourth pair of digits represents the month. The final set of digits is for the year.

For example, the time of 3:06 PM on the date Jan. 31, 1990 should be entered as the following number: 1506310190. Upon entry of the time, the clock/calendar 28 of the electronic controller 18 is reset. The display means 22 will display the time to the user and inquire whether it is correct. If incorrect, the user may re-enter the time and date by pressing the "RESET" key on the touch pad means. Once the correct time and date are entered, the user may proceed with the infusion set up by pressing the "START" key on the touch pad means 20. Again, because the clock is battery powered a user need ony enter the time and date when the apparatus is powered up for the first time or to change the time.

Normal operation begins with a prompt for the user to insert the magnetic media. The prompt remains on screen until information is read. Once the electronic controller 18 has read the information, the name of the IV drug and the stock solution concentration will be displayed on the display means 22.

Next, the display means 22 prompts the user to enter the patient's body weight. The user does so by using the touch pad means 20. After entering the weight in numerical form, the user presses either the LBS or KG key, as appropriate. The electronic controller 18 automatically converts weight entered in pounds into Kgs, the units used in the electronic controller's 18 calculations. This eliminates the possibility of human error in the conversion. The user may correct errors in the entry of the patients weight by pressing the "RESET" key and re-entering the weight. Once the weight is entered correctly, the user presses the "START" key on the touch pad means 20.

In response, to the START, the display means 20 displays the recommended dosage range for the IV drug, and requests that the user enter a desired dosage rate. This eliminates the possibility of human error by relieving the user of the need to know the recommended dosage rate range. By alerting the user to the recommended dosage rate range, the chances of accidentally overdosing a patient are greatly reduced.

The user enters the desired dosage rate via the touch pad means 20. Once entered, the display means 22 displays the desired dosage rate to the user. This allows the user to check for data entry error, and again reduces the possibility of harmful human error. The electronic controller 18 will compare the desired dosage rate to the maximum recommended dosage rate and determine whether the desired dosage rate exceeds the maximum. If so, the display means 22 will inform the user of the condition and request that the user re-enter the desired dosage rate. This double check of the desired dosage rate prevents user error which could result in accidental overdosage. The second time an out-of-range dosage is entered, the electronic controller 18 will accept it. The desired dosage rate will be displayed with asterisks "*" on the display means 22 to indicate the out of range condition. This feature alerts both users and professionals caring for the patient that the patient's reaction to the drug should be closely monitored. A further advantage of this feature is that subsequent users are immediately alerted to the condition.

The electronic controller 18 uses the information provided from the touch pad means 20, patient weight, desired dosage rate, and from the magnetic media reading means 24, stock solution concentration, to calculate the necessary infusion rate. The electronic controller's 18 performance of this calculation further reduces the possibility of human error.

The electronic controller 18 calculates the infusion rate in units of milliliter per hour. Should the user enter the desired dosage rate in units of micrograms of drug per kg of body weight per minute then the electronic controller 18 calculates the necessary infusion rate according to the following formula:

$$\text{infusion rate} = \frac{\text{desired dosage rate} \times \text{body weight} \times 60}{\text{stock solution concentration} \times 1000}$$

The number 60 in the numerator is used to convert minutes into hours and the number 1000 is used to convert from micrograms to milligrams.

Alternatively, should the desired dosage rate be entered in units of milligrams of drug per kilogram of body weight per hour then the formula used by the electronic controller will be:

$$\text{infusion rate} = \frac{\text{desired dosage rate} \times \text{body weight}}{\text{stock solution concentration}}$$

The electronic controller 18 uses integer numbers to perform the series of computations necessary to determine the infusion rate and therefore there is some resolution loss. The order of computations should be arranged to minimize their loss. When properly arranged the resulting infusion rate is off by less than 0.5%. This problem could be alleviated in other embodiments of the invention by using a microcontroller capable of floating point calculations. Such a microcontroller was not used in the preferred embodiment because the IVAC 560 infusion pump employed as the fluid dispensing means 12 accepts only integer values for the infusion rate.

After calculation of the infusion rate, the electronic controller 18 will record the starting time and begin the infusion. As soon as the infusion begins the display means 22 displays the drug name, stock solution concentration, dosage rate, infusion rate and time to complete the infusion. This display remains on screen unless the user requests other information.

During the infusion the electronic controller 18 constantly monitors the actual rate at which drug is infused by the electronically controllable fluid dispensing means 12. During infusion, if the electronic controller 18 detects a difference between the designated and the actual infusion rate, an error condition occurs which halts the infusion until the error is corrected.

During the infusion the user may change the dosage rate, read the pressure of the fluid being infused, read the total volume of fluid infused and total amount of drug dispensed or clear the volume infused. The user may also stop the infusion when desired. These commands are all entered using the touch pad means 20.

Any changes in the infusion are recorded by the electronic controller 18; providing subsequent users with a complete history of the infusion. User commands which do not alter the infusion are not recorded; e.g. read pressure or read volume. Requested information from such commands is displayed for four seconds before the display means 22 returns to its normal display mode during infusion.

The present embodiment of the apparatus offers the user a variety of special function keys. The READ PRES key causes the current infusion pump pressure to be displayed in terms of millimeters of mercury. Pressing the READ VOL key causes the apparatus to calculate and display the total volume of liquid infused, as well the total drug dosage administered. CLR VOL resets to zero the cumulative volume and the total drug dosage. A user can determine the total time a patient has been on infusion, excluding any "hold time", by pressing "START TIME". A user may change the infusion rate by using "SET RATE". The infusion pump may be toggled on and off via "START/STOP". The display will indicate when an infusion has been placed on hold. "RESET" allows a user to restart the apparatus. "RESET" must be used in conjunction with START/STOP to ensure that the pump is no longer in remote.

Another unique feature of the apparatus is that it will not respond to any other keys except those above-mentioned during normal operation.

The following screens are displayed to the user during operation:

Startup:
    PLEASE SWIPE CARD THROUGH READER
After Swipe:
    INPUT PATIENT WEIGHT (END WITH UNITS)
    DOBUTAMINE HYDROCHLORIDE
    250 mg IN 250 cc D5W
After body weight input:
    PRESS START IF CORRECT, RESET IF NOT
    150.lbs
    DOBUTAMINE HYDROCHLORIDE
    250 mg In 250 cc D5W
After pressing START:
    INPUT DOSAGE RATE (END WITH UNITS)
    RANGE 3-15 ug/kg/min
    DOBUTAMINE HYDROCHLORIDE
    250 mg IN 250 cc D5W
After inputting rate:
    PRESS START IF CORRECT, RESET IF NOT
    RAGE 3-15 ug/kg/min 5 ug/kg/min
    DOBUTAMINE HYDROCHLORIDE
    250 mg IN 250 cc D5W
After pressing START:
    PLACE PUMP IN REMOTE MODE
    ON HOLD
    DOBUTAMINE HYDROCHLORIDE    14:08
    250 mg IN 250 cc D5W
Normal operation display:
    CURRENT RATE: 5 ug/kg/min
    19 ml/hr    ON HOLD
    DOBUTAMINE HYDROCHLORIDE    14:10
    250 mg IN 250 cc D5W
Pressure display:
    CURRENT PRESSURE: 003 mmHG
    DOBUTAMINE HYDROCHLORIDE    14:12
    250 mg IN 250 cc D5W
Volume display:
    CUMULATIVE VOLUME INFUSED:    00016 ml
    CUMULATIVE DRUG DOSAGE:    00016 mg
    DOBUTAMINE HYDROCHLORIDE    14:55
    250 mg IN 250 cc D5W
Clear volume display:
    CUMULATIVE VOLUME INFUSED:    00000 ml
    CUMULATIVE DRUG DOSAGE:    00000 MG
    DOBUTAMINE HYDROCHLORIDE    14:58

```
  250 mg IN 250 cc D5W
Start time display:
    TOTAL TIME ON INFUSION:           1:03
    DOBUTAMINE HYDROCHLORIDE         15:10
    250 mg IN 250 cc D5W
After pressing start during normal mode:
    CURRENT RATE:       5 ug/kg/min
    19 ml/hr            INFUSING
    DOBUTAMINE HYDROCHLORIDE         15:12
    250 mg IN 250 cc D5W
```

DETAILED DESCRIPTION OF THE APPARATUS

Figure 2:
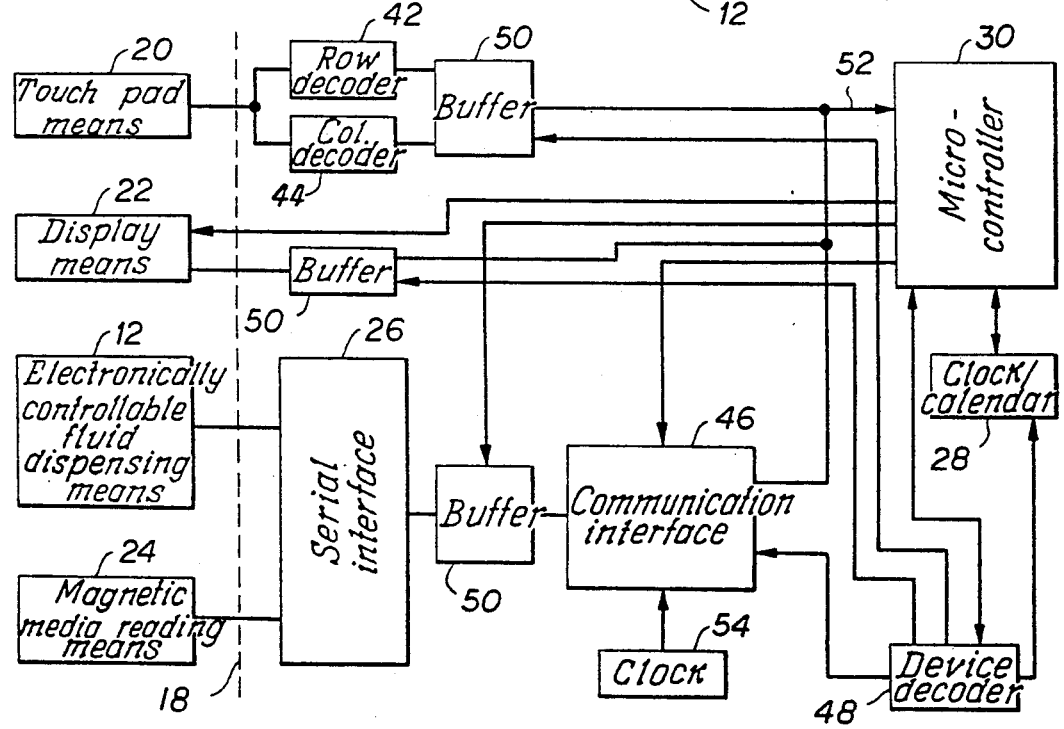
FIG. 2 is a detailed block diagram of the electronic controller and its connections to the various other components of the present invention.

Turning now to FIG. 2, a more detailed block diagram of the invention 10 can be seen. The electronic controller 18 is shown to the right of the broken lines. As previously mentioned, the design of the electronic controller 18 is centered around a microcontroller 30.

A variety of devices control the interface between the microcontroller 30 and the peripheral devices, 20, 22, 24 and 12. However, the data to and from each peripheral device 20, 22, 24 or 12 enters the microcontroller 30 through one 8 bit data bus 52. The microcontroller 30 selects which peripheral device it will read from or write to by using the device decoder 48. The device decoder 48 determines which peripheral device 20, 22, 24 or 12 bus has been selected by the microcontroller 30 and enables the buffers 50 between the display 22 and the touch pad means 20 and the microcontroller 30 and the communication interface 46, as appropriate. Additionally, once the infusion begins, the microcontroller 30 uses the device decoder 48 to read the clock/calendar 28, in order to keep track of the length of the infusion.

The microcontroller 30 directly provides the display means 22 with the signals necessary to clear the display means 30, and to write to specific lines of the display.

As previously mentioned, the magnetic media reading means 24 used is a serial output device, as is the electronic fluid dispensing means 12. In combination, the serial interface 26 and communication interface 46 convert the serial data into parallel data, which the microcontroller 30 uses. The communication interface 46 actually performs the serial-parallel conversions. The serial interface 26 is used to convert the voltage levels from the magnetic media reading means 24 and fluid dispensing means 12 into the voltage levels utilized by the communication interface 46. The buffer 50 is used as a multiplexer with which the microcontroller 30 selects which serial device, magnetic media redding means 24 or electronic fluid dispensing means 12, to communicate with. The clock 54 is used to control the timing of the serial-parallel conversions of the communication interface 46. Through the communication interface 46, the microcontroller 30 directly controls whether it receives or transmits data from the electronically controllable fluid dispensing means 12 or the magnetic media reading means 24.

The touch pad means 20 data output is transformed into a format usable by the microcontroller 30 by the row decoder 42 and the column decoder 44. In the preferred embodiment the touch pad means 20 is a Grayhill 4×4 pad. The output from this pad means 20 is 8 bits, 4 bits indicating the row of the button pushed and 4 bits indicating the column of the button pushed. Each 4 bit signal is converted to a 2 bit signal by the respective decoder, 42 or 44. These two 2 bit signals are combined to form a 4 bit signal by a buffer 50.

Those skilled in the art of electronic controller design will realize that the use of a microcontroller 30 is not the only means of realizing the electronic controller 18. Other designs are possible so long as they are capable of handling the input and output demands of 4 peripheral devices and performing minor computations.

Figure 3A:
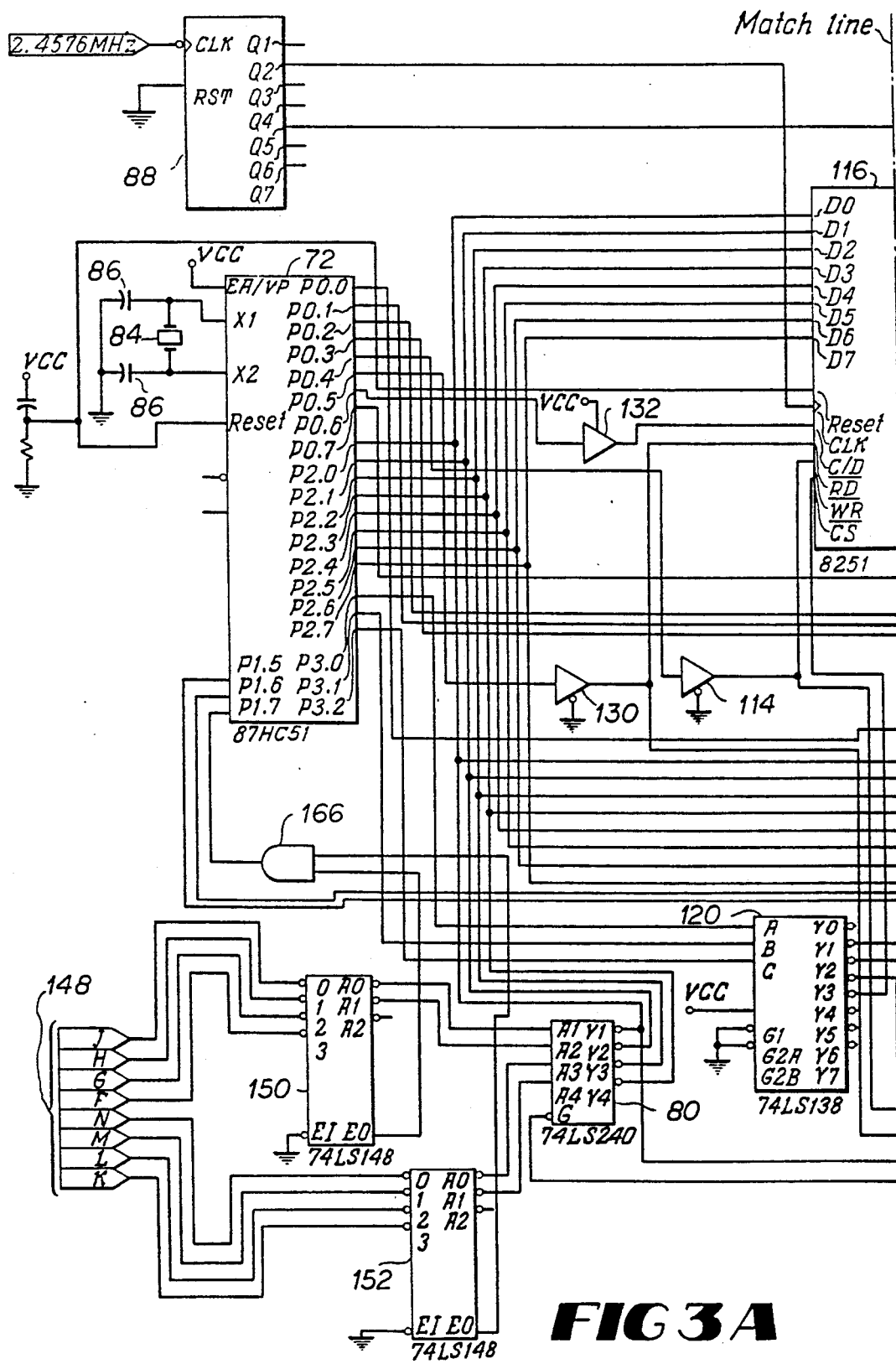
FIGS. 3a and 3b provide a schematic diagram of the preferred embodiment of the electronic controller.
Figure 3B:
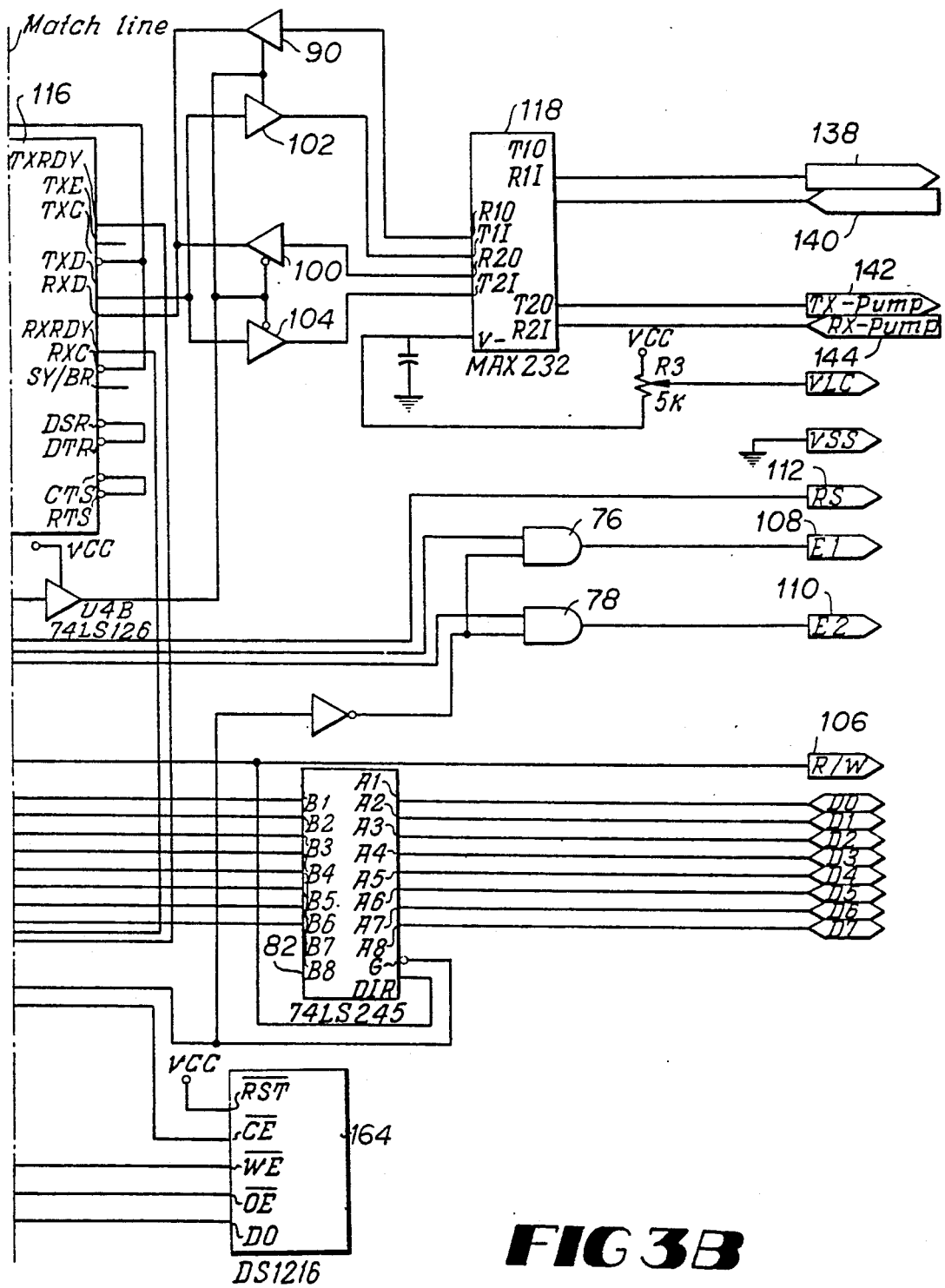

Turning now to FIG. 3, a schematic diagram of the electronic controller 18 can be seen.

The microcontroller 30 used is a 87HC51 72. The 87HC51 72 possesses 4 I/O ports. Port 0, with pins P0.0 through P0.7, is used as a control port. The output of P0.0 is connected to the Read/Write (R/W) control 106 of the LCD. Depending upon the state of R/W 106, the display means 22 can be written to or read from. The 87HC51 72 reads the display means 22 to determine whether it is busy or ready for input.

P0.1 is connected to a first input of a first AND gate 76. LCD select pin $Y_1$, from the device decoder 48 is connected to the second input of the first AND gate 76. In the preferred embodiment, a 74LS138 3 to 8 address decoder 120 is used as a device decoder 48. The output of the AND gate 76 is connected to E1 108 of the LCD. When E1 108 is enabled the 87HC51 72 can write to the top two rows of the LCD. P0.2 is connected to a first input of a second AND gate 78. LCD select pin $Y_1$, from device decoder 48 is connected to second input of the second AND gate 78. The output of the second AND gate 78 is connected to E2 110 input of the LCD. When E2 110 is enabled the 87HC51 72 can write to the bottom two rows of the LCD display. P0.3 is connected to the Register Select (RS) 112 of the LCD. According to the state of RS 112, the 87HC51 72 will write to the LCD's control or data registers. The control registers are written to in order to clear the screen of the LCD. In all other cases, the 87HC51 72 writes to the data registers. P0.4 is buffered through buffer 114, a 74 LS125, a tristate buffer with a low enable. Through buffer 114, P0.4 connects to the Write Enable (WE) of the clock/calendar 164 and the Write (WR) pin of the communication interface 46. When WR is enabled the 87H51 72 can write to the data pins, D0-D7, of the communication interface 46. The communication interface 46 used in the preferred embodiment is an 8251 programmable communication interface 116. P0.5 is connected to the Read (RD) pin of the communication interface 116 through a 74LS125 buffer 130. When RD is enabled the 87HC51 72 can read the data on pins D0-D7 of the programmable communication interface 116. P0.6 is connected through a buffer 132 to the communications Control Data (CD) pin 6. The state of CD lets the Programmable Communication Interface 116 know whether the 87HC51 72 is sending control information or data. P0.7 selects data from either the magnetic media reading means 24 or electronically controllable fluid dispensing means 12. The selection is made according to the state, high or low, of P0.7. When P0.7 is high, it enables tristate buffers 90 and 102 which are connected between the serial interface 26 and the programmable communication interface 116. This allows communication between the magnetic reading means 24 and the programmable communications interface 116. When P0.7 is low it enables tristate buffers 100 and 102 between the Programmable Communications Interface 116 and the serial interface 26. This allows communication between the electronically controllable fluid dispensing means 12 and the programmable communication interface 116.

Port 1 of the 87HC51 72 is used as an input port for control data from the touch pad means 20 and the Programmable Communications Interface 116. Pins P1.0 through P1.4 are unused. P1.5 receives a transmit ready (TXRDY) signal from the Programmable Communications Interface 116, informing the 87HC51 72 that the Programmable Communication Interface's 116 transmit buffer is empty. P1.6 receives a receive ready (RXRDY)signal from the Programmable Communications Interface 116, informing the 87Hc51 72 that the Programmable Communications Interface's 116 receive buffer is full. P1.7 receives a signal from the touch pad means 20 which informs the 87 HC51 72 that a key has been pressed.

Port 2 of the 87HC51 72 is used as a data port. The 87HC51 72 reads and writes to all the peripheral devices 20, 22, 24 and 12 through Port 2. P2.0 is the LSB or the data word, and P2.7 is the MSB of the data word. $Y_1$, $Y_2$, $Y_3$ and $Y_4$ of the keyboard buffer 80, a 74LS240, are connected to P2.0, P2.1, P2.2 and P2.3 of the 87HC51 72. respectively. D0-D7 of the Programmable Communications Interface 116 are connected to P2.0-P2.7. And finally, P2.0-P2.7 are also connected to B1-B8 of the display buffer 82, respectively.

The last port of the 87HC51 72, Port 3, is used as an address port to control which peripheral device 12, 20, 22 or 24 is connected to the data bus, Port 2. Only pins P3.0-P3.2 of this port are used. All three pins are connected to the address decoder 120 74LS138 3 bit to 8 bit decoder. When $P_{32}P_{31}P_{30}=001$ the device decoder selects the display means 22; $Y_1$ of the 74LS138 120 goes low; enabling the display buffer 82. If $P_2P_1P_0=010$, then $Y_2$ of the 74LS138 120 goes low, enabling the clock/calendar 164. If $P_2P_1P_0=011$, the touch pad means buffers are selected by $Y_3$ of the 74LS138 120 going low. The Programmable Communications Interface 116 is selected when $P_2P_1P_0=100$ and $Y_4$ of the 74LS138 120 goes low.

The 87HC51 72 derives its own internal clocks from an external crystal 84. The crystal 84 is connected between pins $X_1$ and $X_2$ of the 87HC51 72. Small capacitors 86 are connected between $X_1$ and ground, and $X_2$ and ground. The selection of the crystal and the capacitors would be obvious to one skilled in the art from reading the data sheets from 87HC51 72.

The Programmable Communications Interface 116 is selected when the CS input goes low. CS is connected to $Y_4$ of the address decoder 120. Clocks for the Programmable Communications Interface 116 are applied at pins CLK, transmit clock (TXC) and receive clock (RXC). All of these clocks are received from a counter 88, which divides down an approximately 2.5 MHZ clock. The counter 88 used is a 74HC4024, 7 bit counter. $Q_2$ of the counter 88 provides a 614KHZ clock to CLK, and $Q_5$ provides a 76.8 KHZ clock to RXC and TXC.

The Programmable Communication Interface 116 receives serial data on pin RXD. This data may come from the magnetic media reading means 24 or the electronically controllable fluid dispensing means 12 depending on which tristate buffer is enabled, 90 or 100.

The Programmable Communication Interface 116 transmits serial data on pin TXD. If tristate state buffer 102 is enabled, the data will be transmitted to the magnetic media reading means 24. On the other hand, if tristate buffer 104 is enabled, the data will be transmitted to the electronically controllable fluid dispensing means 12.

Tristate buffers 90 and 102 are 74LS126 in the preferred embodiment. These are tristate buffers with a high enable. Tristate buffers 100 and 104 are 74LS125, a tristate buffer with a low enable, in the preferred embodiment.

The serial interface 26 used is an MAX232 118. The MAX232 118 communicates with the magnetic media reading means 24 on Port 1. Pin T10 138 is connected to receive port of the magnetic media reading means 24. Pin R1I is connected to the transmit Port 140 of the magnetic media reading means 24. Over Port 2, the MAX232 118 communicates with the electronically controllable fluid dispensing means 12. Pin T20 connects to the receive Port 142 of the electronically controllable fluid dispensing means 12. Pin R2I connects to the transmit Port 144 of the electronically controllable fluid dispensing means 12.

The MAX232 118 receives on Pin T1I serial data to be transmitted to the magnetic media reading means 24. Pin T1I is connected to the output of buffer 102. The MAX232 118 passes on serial data from the magnetic media reading means 24 on Pin R10. R10 is connected to the input of buffer 90. Data received from the electronically controllable fluid dispensing means 12 is output of pin R20 of the MAX232 118. Pin R20 is connected to the input of buffer 100. Data to be transmitted to the electronically controllable fluid dispensing means 12 is provided to the MAX 232 on Pin T2I. Pin T2I is connected to the output of buffer 104.

The buffer used to buffer the parallel data to and from the LCD is a 74LS245 82. Pins $A_1$-$A_8$ of the buffer 82 are connected to the LCD data bus 146. Pins $B_1$-$B_8$ of the buffer 82 are connected to data port, Port 2, of the 85HC51 72.

In the preferred embodiment, the touch pad means 20 is a Grayhill 4×4 key pad. This keypad provides an 8 bit output 148. Each of the 16 buttons is uniquely identified by its row and column location, 4 bits indicating row and 4 bits indicating column. The combination of row 42 and column 44 decoders convert each 8 bit number into a four bit number, which uniquely identifies each button according to a number. Grayhill outputs J, H, G and E each represent a row location; these connect to a 74LS148 150, an 8-3 priority encoder. Similarly, Grayhill outputs N, M, L and K, each represent a column location, and connect to a 74LS148 152.

Encode input pins (EI) for both the row 50 and column decoders are constantly enabled, allowing data to move in at anytime. When the row or column location of a button has been encoded the encode out (EO) pin goes high, signalling that the data is ready. The EO output from each decoder 150 is AND'd together through AND gate 166. A high output from the AND gate 166, signals the 87HC51 72 that a button has been pushed. The 87HC51 72 receives this information on P1.7. The 87HC51 72 can then determine which button was pushed by enabling the key board buffer 80 and reading the data at Port 2.

In the preferred embodiment, the clock/calendar 28 is a D1216 a real time clock/calendar chip 164. The reset pin (RST) is active low, and is tied high to prevent reset. The 87HC51 72 can write to the clock/calendar chip 164 by enabling the write enable pin (WE). The WE pin is controlled by P0.4 of the 87HC51 72 through a buffer 114. The 87HC51 72 may read the time from the clock/calendar 164 by first enabling the output enable pin (OE). The OE pin connects to P0.5 of the 87HC51 72 through a buffer 130. Data is exchanged serially between the two devices, 72 and 164, via the connection of D0 of the clock/calendar 164 to P2.0 of the 87HC51 72. The DS1216 is always running, CE of the clock/calendar 164 is connected to pin Y2 of decoder 120. CE is used when the 87HC51 72 reads or writes data from the DS1216 164.

A person skilled in the art will realize that other designs of the electronic controller 18 are possible in addition to the preferred embodiment, and that there are alternative ways of realizing the electronic controller design chosen.

We claim:

1. An electronic fluid flow rate controller for controlling an electronically controllable fluid dispensing means which in turn controls the infusion of an intravenous drug into a patient, wherein the improvement comprises:
   a prerecorded data storage means containing prerecorded data identifying said drug and information about said drug;
   patient information means for receiving information characteristic of said patient's weight who is to receive said drug and for generating an input therefrom;
   input means for automatically reading said information about said drug from said data storage means and for receiving said input from said patient information means and for thereafter automatically generating first signals pertaining to such information about said drug and information characteristic of said patients weight;
   control means for receiving said first signals and thereafter generating a second signal derived from said first signals and which is indicative of a prescribed rate at which said drug is to be dispensed; and
   means for transmitting said second signal from said control means to said fluid dispensing means for actuating said fluid dispensing means to deliver said drug at a rate dictated by said second signal.

2. The electronic fluid flow rate controller defined in claim 1, wherein said electronically controllable fluid dispensing means provides to said control means a third signal proportional to the actual infusion rate, said control means modifying said second signal in response to said third signal such that the actual infusion rate is substantially equal to the desired infusion rate.

3. The electronic fluid flow rate controller defined in claim 2 further comprising a clock internal to said control means; said clock enabling said control means to monitor said fluid dispensing means and control the total infusion time and the total amount of drug infused by said fluid dispensing means, into the patient; including means for transmitting to said means for transmitting information from said control means to said display means, a query as to the data and time; said means for automatically reading information, transmitting signals as to the date and time information, entered by a user to said input means, said control means using the date and time information to set said internal clock.

4. The electronic fluid flow rate controller defined in claim 3 wherein the functions performed by said control means after receiving signals pertaining to the date and time include retransmits said signals pertaining to the date and time and retransmitting a query as to their correctness, to said display means;
   the function of said display means includes displaying to the user, the query as to the correctness of the date and time entered; and
   the function of said control means includes resetting said internal clock in response to the reset request and receiving a second date and time from said input means.

5. The electronic fluid flow rate controller defined in claim 3 wherein the functions performed by the control means further comprise modifying said second signal such that the infusion stops, in response to a "Stop" request entered by a user into said touch pad.

6. The electronic fluid flow rate controller defined in claim 1 wherein:
   said data storage means containing prerecorded indicia is a separate magnetic media removeably positioned for access by said controller; and wherein said input means includes reading means for automatically reading data about said drug from said prerecorded indicia and for generating a portion of said first signal in response to the data which is read.

7. The electronic fluid flow rate controller defined in claim 6 wherein said reading means comprises a magnetic media reader for reading said storage data from said magnetic media.

8. The electronic fluid flow rate controller defined in claim 7 wherein said magnetic media includes a magnetic card and, and wherein said magnetic media reader is a magnetic card reader for reading said magnetic card.

9. The electronic fluid flow rate controller defined in claim 6 wherein said input means includes a touch pad means.

10. The electronic fluid flow rate controller defined in claim 6 wherein said input means generates, as a portion of said first signals, signals which are indicative of the stock solution concentration of the intravenous drug, the patient's weight, and the desired dosage rate.

11. The electronic fluid flow rate controller defined in claim 1 further comprising:
    display means for displaying to a user information read by said input means; and
    means for transmitting such information from said control means to said display means.

12. The electronic fluid flow rate controller defined in claim 11 wherein said data storage means stores data indicative of the stock solution concentration and a desired infusion rate of said drug, said display means displaying said information as a normal display when the intravenous drug infusion begins, and continuing to display said normal display until said display means receives other signals from said control means.

13. The electronic fluid flow rate controller defined in claim 12 including means wherein said display means is returned to said normal display after displaying for a fixed period of time said information carried by said other signals.

14. The electronic fluid flow rate controller defined in claim 13 including means for controlling said fixed period of time to about four seconds.

15. The electronic fluid flow rate controller defined in claim 13 wherein said information carried by said other signals includes signals indicating the name of the intravenous drug and a warning specific to the intravenous drug.

16. The electronic fluid flow rate controller defined in claim 15 wherein said input means includes a touch pad means for providing signals relating to the weight of said patient, as part of the characteristics of the patient for forming a part of said first signals which are transmitted to said control means and are displayed by said display means.

17. An electronic fluid flow rate controller for controlling an electronically controllable fluid dispensing means which in turn generates signals which control the infusion of intravenous drugs to a patient wherein the improvement comprises:

a magnetic media having recorded therein information about an intravenous drug including, the name of the drug, the stock solution concentration of the drug and the recommended dosage range of the drug;

magnetic media reading means for reading said magnetic media and for generating information signals indicative of said name, said stock solution concentration, and said recommended dosage range of said drug;

patient information means including touchpad means for generating touchpad signals relating to the patient's weight and the desired rate of infusion of the drug;

display means for displaying said information relating to said name, said stock solution concentration, and said recommended dosage range of said drug; and a controller for receiving said touchpad signals from said touch pad means, and for receiving information signals from said magnetic media reading means generating control signals as a function of said touchpad signals and said information signals and for transmitting said control signals to said electronic controllable fluid dispensing means; and indicating means for transmitting a signal for indicating if the desired rate of infusion exceeds the recommended dosage range.

* * * * *